United States Patent [19]
Nilsson et al.

[11] Patent Number: 5,504,092
[45] Date of Patent: Apr. 2, 1996

[54] USE OF LINOMIDE TO INCREASE HEMOPOIETIC CELL PRECURSORS

[75] Inventors: Bo Nilsson, Helsingborg; Terje Kalland, Löddeköpinge; Birgitta Termander, Helsingborg, all of Sweden

[73] Assignee: Pharmacia AB, Stockholm, Sweden

[21] Appl. No.: 222,002

[22] Filed: Apr. 4, 1994

Related U.S. Application Data

[63] Continuation of Ser. No. 934,471, Sep. 11, 1992, abandoned.

[30] Foreign Application Priority Data

Mar. 27, 1990 [SE] Sweden ................... 9001111.5

[51] Int. Cl.$^6$ .................................................. A61K 31/47
[52] U.S. Cl. .................................................. 514/312
[58] Field of Search ............................... 514/312

[56] References Cited

U.S. PATENT DOCUMENTS 4,547,511 10/1985 Kriksoo et al. ................... 514/312

OTHER PUBLICATIONS

Kalland et al., Chem Abstracts CA103(15):115873z, 1985.
Larsson, E. L., Joki, A. L. and Stalhandske, T., Int. J. Immunopharmacol. 9:425, 1987.
Kalland, T., Alm, G., And Stalhandske, T., J. Immunol. 134:3956, 1985.
Stalhandske, T., And Kalland, T., Immunopharmacol. 11:87, 1986.
Tarkowski, A., Gunnarson, K., And Stalhandske, T. Arthritis And Rheum. 29:1405, 1986.
Kalland, T., Cancer Res. 46:3018, 1986.
Kalland, T., J. Immunol. 137:2268, 1986.
Bengtsson, M., Tötterman, T. H., Smedmyr, B., Festin, R., Öberg, G. And Sominnsson, B., Leukemia 3:68, 1989.
Vassil St Georgiev, Trends In Pharmacological Sciences, vol. 9, No. 12, 1988, pp. 446–451.
TH Tötterske, et al., Bone Marrow Transplant 5 (Suppl. 2). 1990. 92, p. 171.
M. Bengtsson, et al., Scand J. Immunol 32 (4). 1990, 384.
B. Gerdin, et al., Transplantation Proceedings, vol. 21, No. 1, 1989, pp. 853–855.
A. Wanders, et al., Transplantation Proceedings, vol. 21, No. 1, 1989, pp. 853–855.

*Primary Examiner*—Raymond Henley, III
*Assistant Examiner*—William R. A. Jarvis
*Attorney, Agent, or Firm*—Pravel, Hewitt, Kimball, & Krieger

[57] ABSTRACT

The present invention concerns the use of Linomide, i.e. N-phenyl-N-methyl-1,2-dihydro-4-hydroxy-1-methyl-2-oxo-quinoline-3-carboxamide for the treatment of humans subjected to BMT, cytostatic treatment irradiations or combinations thereof.

14 Claims, 8 Drawing Sheets

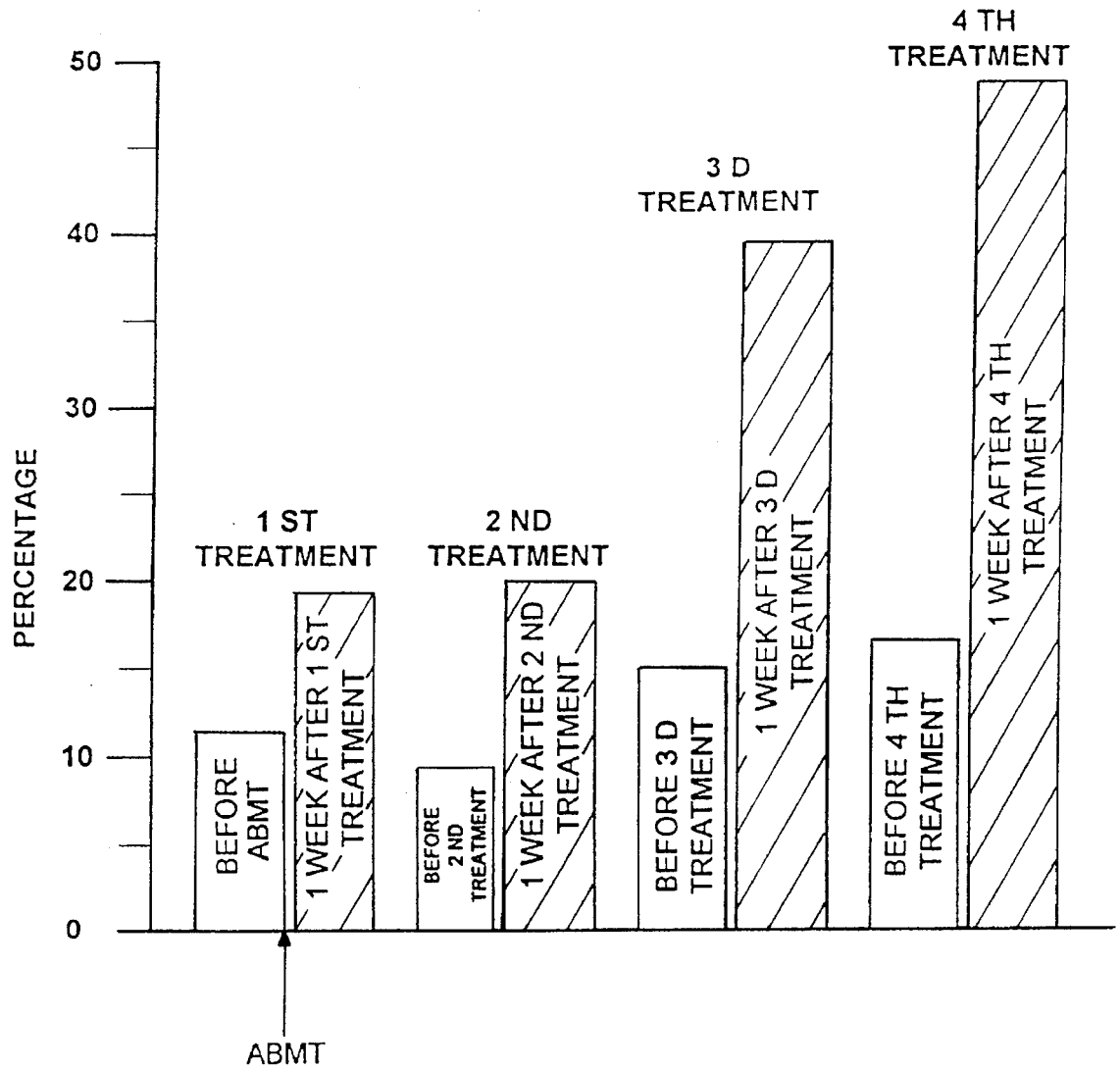

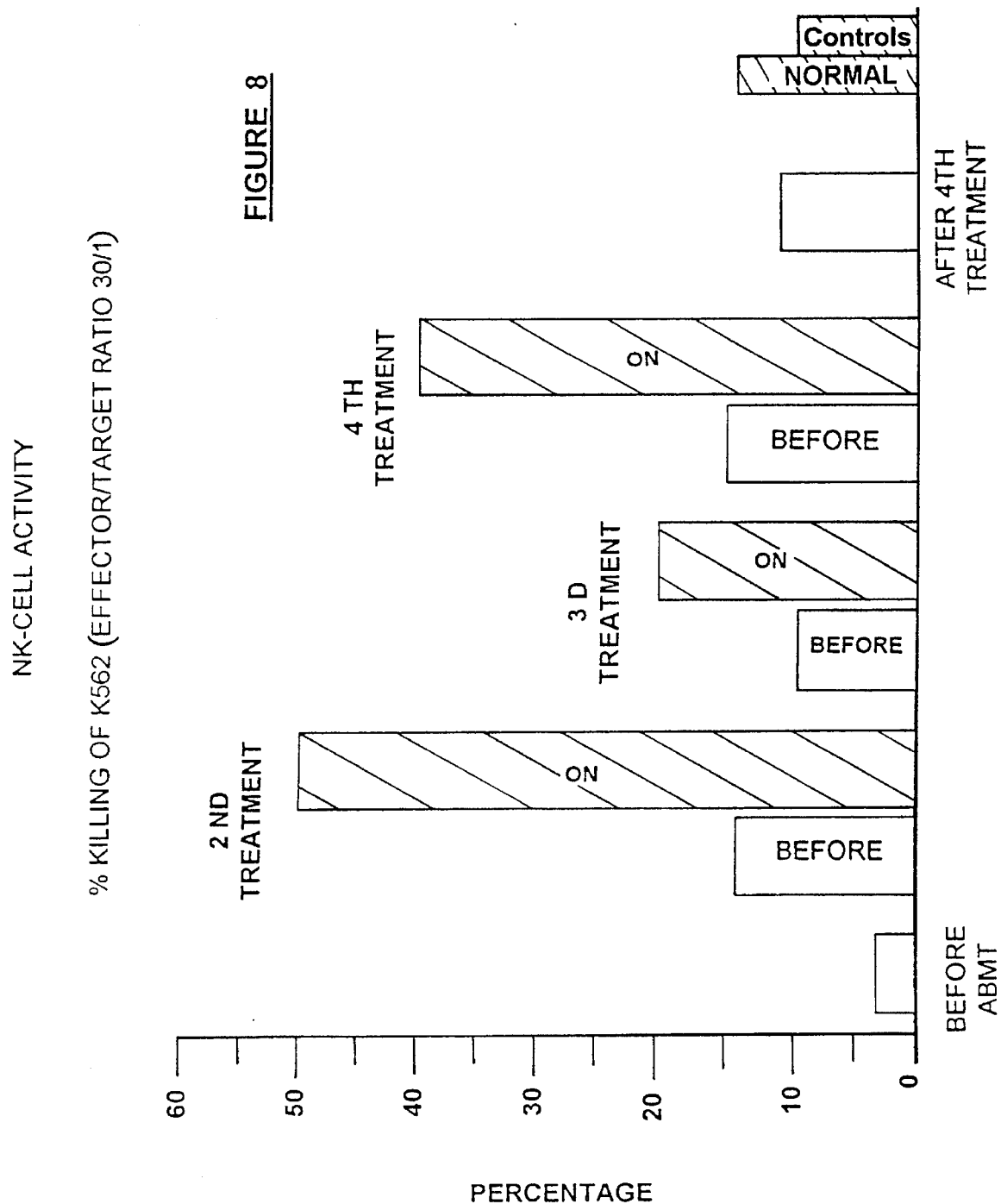

USE OF LINOMIDE TO INCREASE HEMOPOIETIC CELL PRECURSORS

This is a continuation of application Ser. No. 07/934,471 filed on Sep. 11, 1992 now abandoned.

The present invention concerns the use of Linomide or a pharmaceutically acceptable salt thereof for the treatment of humans subjected to bone marrow transplantation, cytostatic treatment, irradiations or combinations thereof.

BACKGROUND OF THE INVENTION

Bone marrow transplantation (BMT) has progressed during the past 15 years from a procedure to be undertaken only as a last desperate measure to a therapeutically effective modality for the treatment of selected patients with malignant disease.

As is generally known the dose of most antineoplastic chemotherapeutic agents that may be administered is limited largely by the toxicity to the normal marrow. The availability of donor marrow for transplantation, however, makes it possible to administer chemoradiotherapy in supralethal doses in an effort to kill a greater fraction of the malignant cells and to use the donor marrow to save the patient from iatrogenic death. The infused marrow will reconstitute the host's hematopoietic and immunologic systems. In addition, if the immune system of the transplanted marrow can exert an antitumor effect, marrow transplantation also may represent a form of adoptive tumor immunotherapy.

An autologous marrow graft refers to the patient's own marrow that has been obtained and usually cryopreserved and reinfused after the patient has received supralethal chemoradiotherapy. A syngeneic marrow is obtained from a donor who is a genetically identical twin, and an allogeneic marrow is obtained from a donor of different genetic origin.

Cancer patients are frequently treated by a regimen of high-dose chemotherapy or total body irradiation (TBI) which are used to eradicate the malignant cells. Most preparative regimens have included supralethal TBI because it has an antitumor effect, can penetrate privileged sites for tumor (e.g., CNS and testicle) where chemotherapy is ineffective, and is sufficiently immunosuppressive to allow engraftment.

The most commonly used regimen has consisted of cyclophosphamide (60 mg/kg/day IV) for 2 consecutive days, followed by a supralethal dose of TBI, usually 1000 rad, delivered at 5 to 8 rad/min, or 200 to 225 rad/day for 6 to 7 days. Marrow is infused within 24 hours after the last dose of TBI.

The first 3 or 4 weeks after grafting are critical because the chemoradiotherapy has eradicated all normal marrow function and there is a time lag before detectable cell production by the infused marrow occurs. The granulocyte count usually rises to 500 $mm^3$ after 2 to 4 weeks. Platelet production generally takes slightly longer. Until that time the patient requires supportive care, with appropriate use of transfusions and antibiotics.

SUMMARY OF THE INVENTION

According to the present invention it has now surprisingly been shown that N-Phenyl-N-methyl-1,2-dihydro-4-hydroxy-1-methyl-2-oxo-quinoline-3-carboxamide has properties that might be useful for the treatment of a living body subjected to bone marrow transplantation, cytostatic treatment, irradiation or combinations thereof.

Linomide®, the chemical name of which is N-phenyl-N-methyl-1,2-dihydro-4-hydroxy-1-methyl-2-oxo-quinoline-3-carboxamide, was first described in the U.S. Pat. No. 4,547,511 as an immunostimulating agent. This agent, which is also known under the generic name roquinimex, can also be used in the form of a pharmaceutically acceptable salt such as the Na or Ca salt.

Linomide has been shown to have potent immunomodulating properties in a variety of mouse and rat models (E. L. Larsson, A. L. Joki and T. Stalhandske, *International Journal of Immunopharmacology*, 1987, 9:425; T. Kalland, G. Alm, and T. Stalhandske, *J. Immunology*, 1985, 134:3956; T. Stalhandske and T. Kalland, *Immunopharmacology*, 1986, 11:87; A. Tarkowski, K. Gunnarson and T. Stalhandske, *Arthritis and Rheumatism*, 1986, 29:1405; T. Kalland, *Cancer Research*, 1986, 46:3018) as well as in initial clinical studies. It also enhances the delayed hypersensitivity reaction, the ability of lymphocytes to respond to T and B cell mitogens and has adjuvant like effects on antibody production. A prominent feature of Linomide is its ability to stimulate the Natural Killer (NK) cell activity in various organs.

The primary mechanism of action of Linomide has not been elucidated. However, analysis of Linomide's effect on mouse NK cells did unexpectingly show that its mechanism of action is distinct from that of any of the described synthetic immunomodulators.

In pilot trials in humans it has now unexpectedly been found that Linomide has a beneficial effect on the regeneration of lymphoid cells after bone marrow transplantation.

According to the invention Linomide can be administered per os, intramuscularly or parenterally with doses varying from 0.01 to 10 mg/kg preferably 0.05 to 1 mg/kg and most preferably from 0.2 to 0.3 mg/kg body weight given daily or as seldom as bi-monthly, and most preferably twice weekly.

The compositions used for clinical trials could e.g. be the following:

| Composition I | |
|---|---|
| Roquinimex | 10 mg |
| Lactosum | 100 mg |
| Amylum maydis | 60 mg |
| Aqua purificata | 25 mg* |
| Avicel PH 102 | 20 mg |
| Kollidon 30 | 5 mg |
| Sterotex regular | 5 mg |
| Composition II | |
| Roquinimex | 5 mg |
| Lactosum | 105 mg |
| Amylum maydis | 60 mg |
| Aqua purificata | 25 mg* |
| Avicel PH 102 | 20 mg |
| Kollidon 30 | 5 mg |
| Sterotex regular | 5 mg |

*Disappears from the formulation during the course of manufacture.

Other compositions are disclosed in the U.S. Pat. No. 4,547,511 mentioned above and incorporated herein by reference.

EXAMPLES

I. Animal experiments

To determine the effect of Linomide on the regeneration of lymphoid cells after their depletion, NK activity in spleen of mice was followed after exposure to Cyclophosphamide or irradiation.

Animal treatment

All animals used were 5- to 8-week old C57Bl/6 mice obtained from Gamle Bomholtgaard, Ry, Denmark.

Linomide (LS 2616; Pharmacia LEO Therapeutics AB, Helsingborg, Sweden), was continuously administered to the mice in their drinking water corresponding to a daily dose of 160 mg/kg body weight. This dosage regimen has earlier been found to be optimal for stimulation of NK activity. In syngeneic bone marrow transplantation experiments, recipients were irradiated with 800 rad and within 4 hrs injected i.v. with $2\times10^7$ syngeneic bone marrow cells prepared as described below. Cyclophosphamide (Sendoxan: Pharmacia, Uppsala, Sweden) was administered as a single i.p. injection of 300 mg/kg body weight.

Cell preparations

Bone marrow cells were prepared by flushing tibia and femur with ice-cold RPMI 1640 (Flow Laboratories, Irvine, Scotland) supplemented with 25 mM Hepes, 2 mM L-glutamine, $5\times10^{-5}$M 2-mercaptoethanol, 10% fetal calf serum (Flow Laboratories) and penicillin/streptomycin (100 /ug/ml) (complete medium). Spleen cells were prepared by teasing the spleens through a stainless steel mesh. Red blood cells were removed from the spleen cell preparation by hypotonic shock treatment as detailed earlier (T. Stalhandske & T. Kalland, *Immunopharmacology*, 1986, 11:87).

Cytotoxicity assay

Cells to be tested for NK activity were examined in a conventional $^{51}$Cr release assay against YAC-1 target cells as detailed earlier (T. Stalhandske and T. Kalland, *Immunopharmacology*, 1986, 11:87). In brief, $5\times10^3$ $^{51}$Cr-labeled target cells were incubated with 100:1, 50:1 and 25:1 effector cells in 200 ul complete medium for 4 hours and the released amount of $^{51}$Cr in 100 ul of the supernatant determined in a LKB 1272 Clinigamma counter. Percent specific cytotoxicity was determined as $$\frac{\text{test } cpm - \text{spontaneous } cpm}{\text{total } cpm - \text{spontaneous } cpm} \times 100$$

Spontaneous release was determined by incubation of target cells in medium only and total release by incubation in 0.1% SDS.

Bone marrow cultures $5\times10^5$ bone marrow cells separated as described above were cultured in 200 ul complete medium supplemented with optimal (40 U/ml) or suboptimal (10 U/ml) concentrations of rIL-2 for 4 days as described earlier (T. Kalland, *Journal of Immunology*, 1986, 137:2268). Cultures were incubated in round bottom 96 well microtiter-plates.

Linomide dissolved in complete medium was added at the start of the cultures at concentrations indicated in the Results section.

Cultures of spleen cells from the same mice were run in parallel. In brief, $5\times10^6$ cells per ml in complete medium were cultured for 4 days in the presence of 10 U/ml rIL-2 and various concentrations of Linomide.

Statistical analysis

All data were analysed by the Mann-Whitney test.

RESULTS

A strong depression of NK activity was found after impairment of hematopoietic tissue with a single high dose cyclophosphamide. Linomide exposed mice showed a slightly better retaining of NK activity, a significantly faster recovery of NK activity and higher level of NK activity than the control mice (FIG. 1).

The effect of Linomide on the recovery of NK cells after lethal irradiation and syngeneic bone marrow transplantation was followed in a similar manner (FIG. 2). NK activity could be detected in the spleen of the bone marrow recipients at day 6 after transplantation. The recovery was clearly more slow than after depletion with cyclophosphamide although full recovery was reached at about day 12 in Linomide treated and day 14 in the control animals. The level of NK activity comparable to that of fully recovered control mice was obtained at day 10 in Linomide treated mice.

To directly examine the effect of Linomide on NK cell progenitors, limiting dilution analysis of the frequency of bone marrow cells capable of developing into lytically active NK cells in vitro in the presence of IL-2 was performed. Treatment of mice for 4 days with Linomide increased the frequency of bone marrow NK cell precursors from 1/11,900 to 1/6000 (FIG. 3).

A culture system was recently described which enabled the generation of mature NK cells from lytically inactive bone marrow progenitors in the presence of IL-2 (T. Kalland, *Journal of Immunology*, 1986, 137:2268). The effect of Linomide in vitro was examined in this culture system (FIG. 4). Linomide alone in the absence of IL-2 was not able to support the maturation of NK cells as judged by the appearance of cytotoxic activity. Furthermore, Linomide did not enhance the strong cytotoxic activity in bone marrow cultures in the presence of optimal (40 U/ml) amounts of IL-2. However, at suboptimal IL-2 concentrations (10 U/ml), Linomide at concentrations between 1 and 50 ug/ml significantly augmented cytotoxic activity. No effect of Linomide on mature NK cells from spleen cultured with or without IL-2 could be detected.

II. Patient studies

As part of an open pilot phase II-study on patients with Acute Myelogen Leukemia in remission the effect of Linomide on the regeneration of haematopoietic cells after autologous bone marrow transplantation was studied.

Harvest of bone marrow

1–2 months prior to marrow infusion the patients marrow was aspirated to an amount of 15 ml/kg body weight. The marrow was concentrated and stored at $-196°$ C. until the day of reinfusion.

Procedures before infusion

Day 11: central venous cateter was applied. Blood sampling was made as well as judgement of remission. Treatment with ovirax (Acyclovir) was started.

Day 10: Fenantoin (fenytoin)—therapy was started. Patient was isolated.

Day 8 to day 5: Myeleran (Busulphan) 1 mg/kg p.o. every 6th hour.

Day 4: Cyclophosphamide 60 mg/kg i.v., infusion of Uromitexan 24 mg/kg×4. Prophylactic treatment against infections started.

Day 3: Cyclophosphamide and Uromitexan as day 3.

Day 2: Fenantoin- and Zyloric-therapy was terminnated.

Day 0: The marrow was quickly thawed and reinfused. Prior to infusion Soly-Glyc (hydrocortison) 100 mg i.v. was given.

Dosage of Linomide 0.3 mg/kg body weight was given once weekly for periods of 3 weeks intermittent with 3 weeks without the drug. Treatment was started at the time of bone marrow transplantation.

Immunological analysis

The phenotype of mononuclear cells was analyzed in Ficoll-Paque separated from peripheral blood before BMT and at the end of each 3 week cycle with or without Linomide. 2 color FACS-analysis was performed as described earlier (M. Bengtsson, T. H. Toherman, B. Smedmyr, R. Festin, G. Oberg, and B. Sominnson, *Leukemia*, 1989, 3:68) with the following monoclonal antibodies: Leu-M3, HLA-DR, Leu-1, Leu-12, Leu-16, Leu-11, Leu-19, Leu-3, Leu-4.

Cytotoxic activity of peripheral blood mononuclear cells against the NK-sensitive K-562 cell line was determined in a conventional $^{51}$Cr-release assay as described above.

RESULTS

A clear enhancement of the number of cells with NK-phenotype (CD 56) as well as the cytotoxic activity against K-562 was seen in patient 1 (FIGS. 5,6) and patient 2 (FIGS. 7,8) at the end of periods on Linomide treatment. In contrast, the frequency of NK cells as well as NK activity was lower at the end of all intervals without Linomide. Thus, Linomide enhanced the number of mature NK cells following bone marrow transplantation.

III. Patient studies

Five adults (3 males, 2 females, ages 48–57 years) with AML undergoing ABMT in first complete remission were studied. Prior to ABMT, all patients were conditioned with Busulphan (16 mg/kg) and Cyclophosphamide (120 mg/kg) followed by infusion of autologous thawed marrow cells.

Treatment schedule

Linomide was given orally in aqueous solution starting on the day of marrow infusion. The dose was 0.3 mg/kg once a week during the first three weeks, followed by three weeks off therapy. This cyclic treatment with three weeks on/three weeks off Linomide was continued for up to 6 months.

Altogether, the study disclosed that Linomide therapy after ABMT may be beneficial to the patient with regard to leukemia-free survival and infectious complications. The observed effects are of the same order of magnitude as described after IL2 infusion, but side effects were considerably milder. Linomide has the additional benefit of being an oral drug that is easily administered on an out-patient basis.

BRIEF DESCRIPTION OF THE DRAWINGS

FIG. 7: Frequency of CD 56 positive cells in peripheral blood of patient 2 before and at different time after autologous bone marrow transplantation. on=at the end of a 3 week Linomide treatment, off=at the end of a 3 week treatment free interval.

FIG. 8: Cytotoxic activity against K-562 of peripheral blood lymphocytes from patient 2 before and at different time after autologous bone marrow transplantation. on=at the end of a 3 week Linomide treatment, off=at the end of a 3 week treatment free interval. Effector:target ratio 30:1.

REFERENCES

Figure 1:
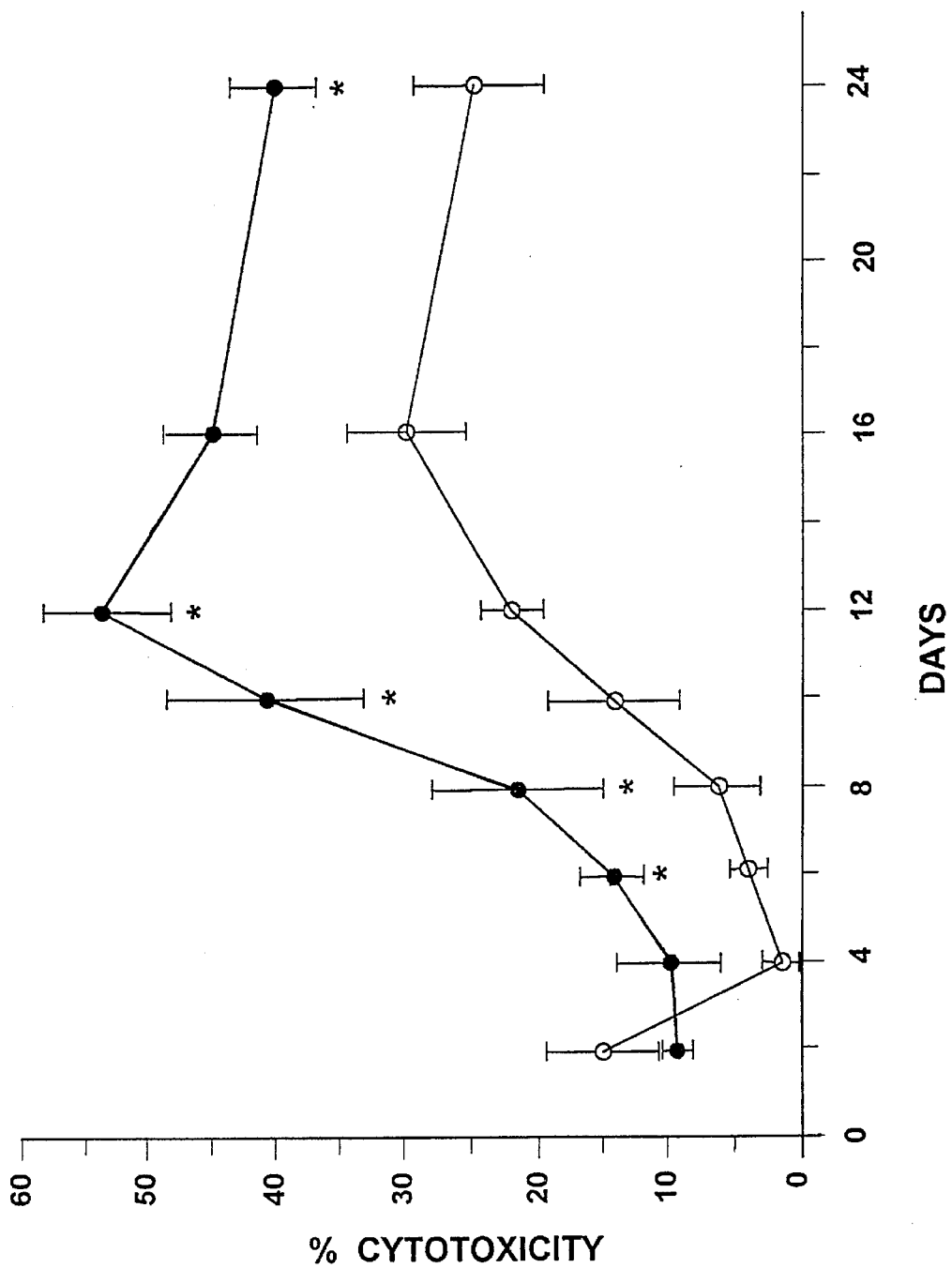
FIG. 1: Effect of Linomide on the regeneration of NK activity in spleen after a single injection of cyclophosphamide. o—o, control; ●—● Linomide treated mice.*p<0.05. Results from a single experiment with 24 mice per group.
Figure 2:
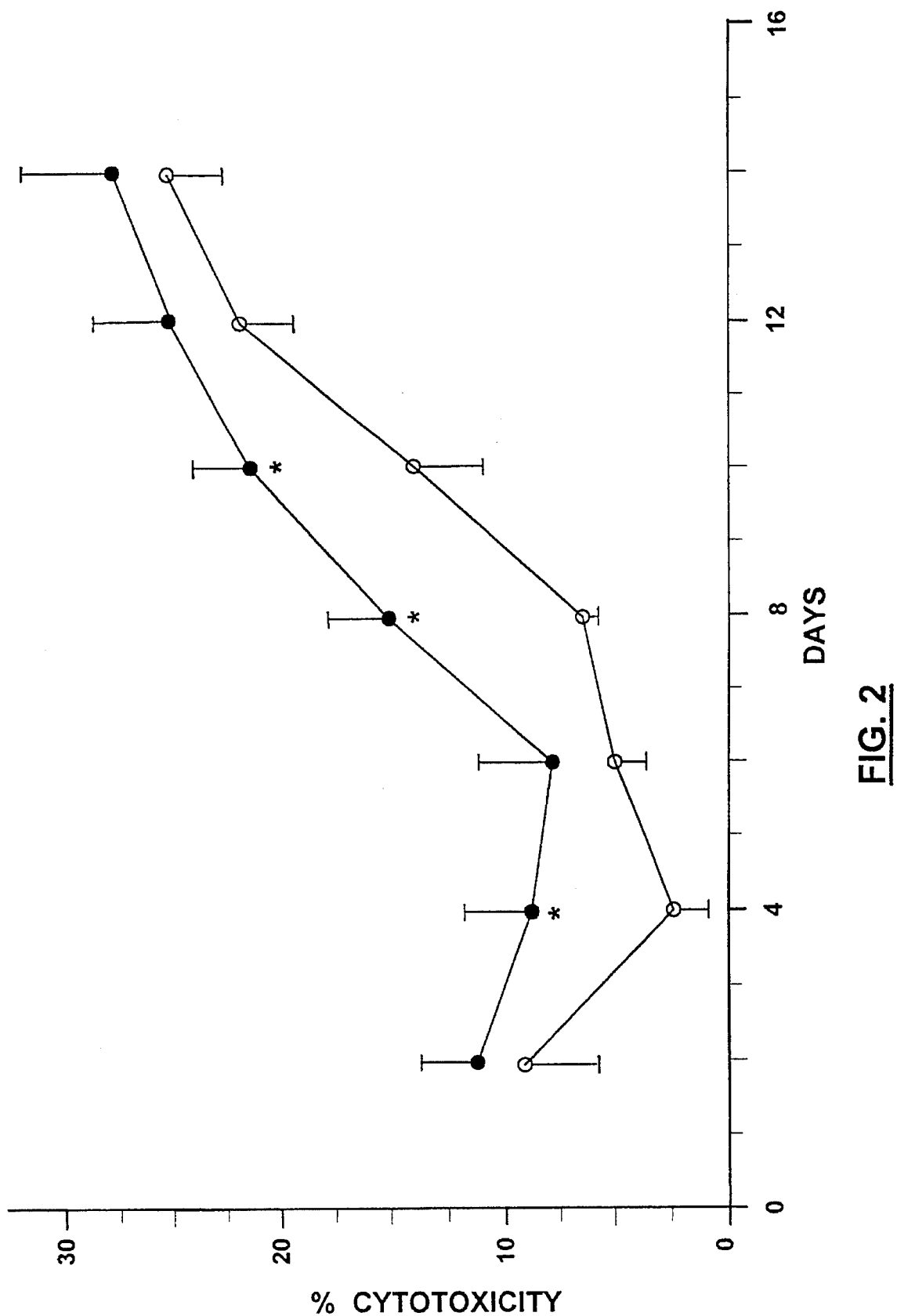
FIG. 2: Effect of Linomide on the regeneration of NK activity in spleen after lethal irradiation and syngeneic bone marrow grafting. o—o, control; ●—● Linomide treated mice.*p<0.05. Results from 1 of 2 similar experiments with 21 and 19 animals per group.
Figure 3:
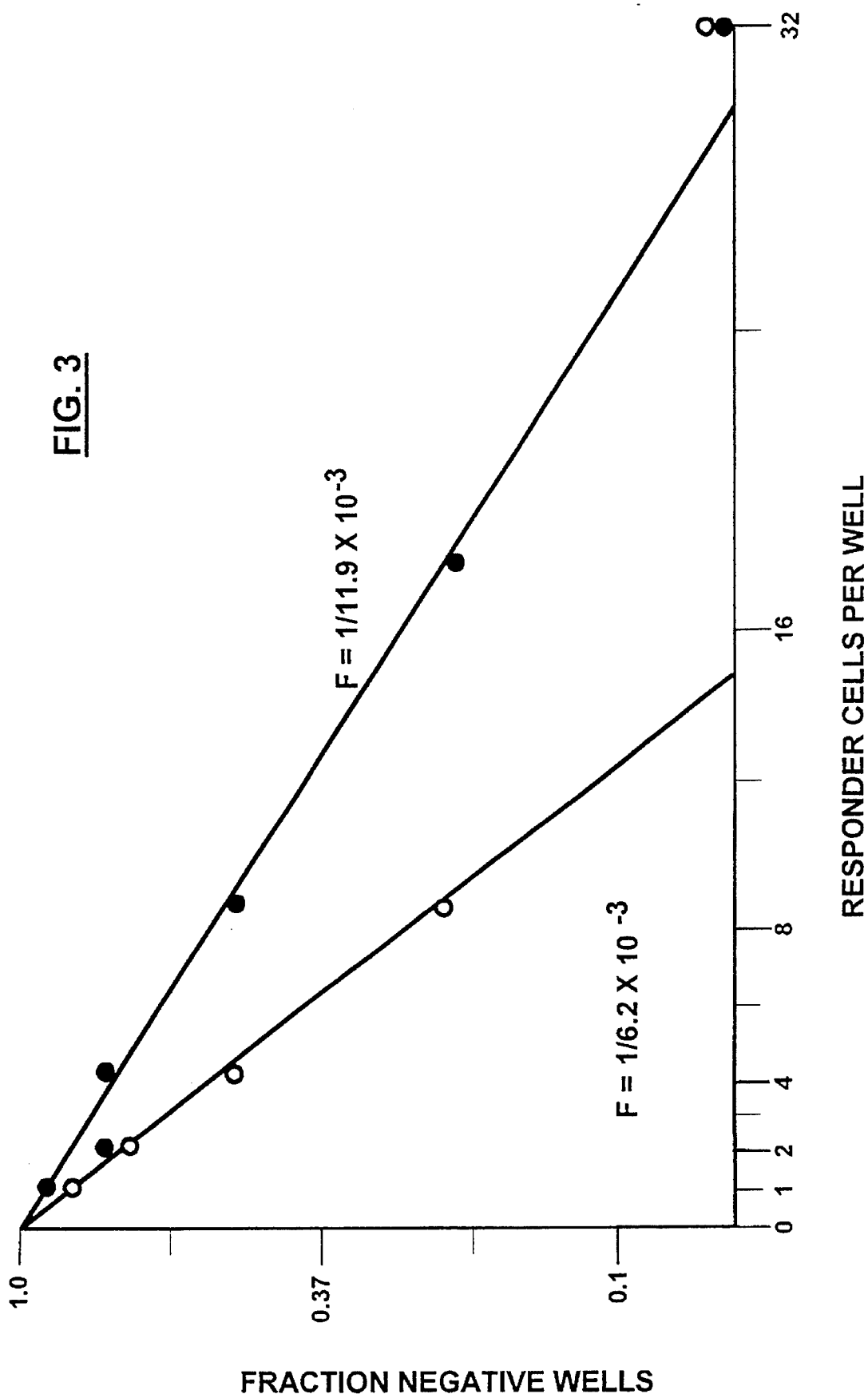
FIG. 3: Limiting dilution analysis of the frequency of NK cell progenitors in bone marrow of control or Linomide treated (160 mg/kg/day for 4 days) mice. o—o control; ●—● Linomide treated mice.*p<0.05. Results from 1 of 3 experiments with consistent results.
Figure 4:
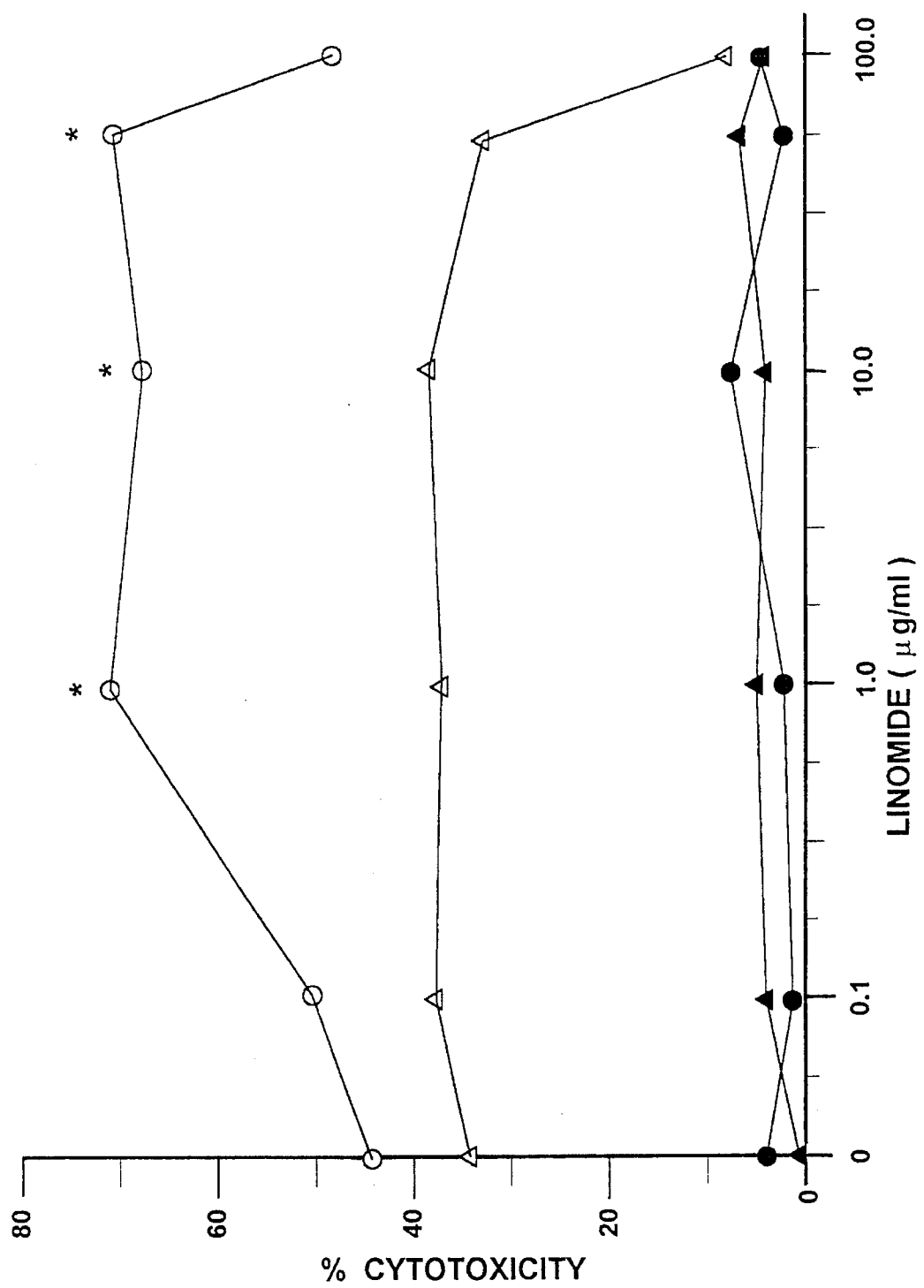
FIG. 4: Effect of Linomide in vitro in NK activity in cultures of bone marrow or spleen cells. Open symbols, cultures supplemented with 10 U/ml IL-2, closed symbols, no IL-2. Circles, bone marrow cells, triangles, spleen cells. Cells were examined for cytotoxicity against YAC-1 cells after culture for 3 days. E: T ratio 100:1. *p<0.05. Results from 1 of 2 similar experiments.
Figure 5:
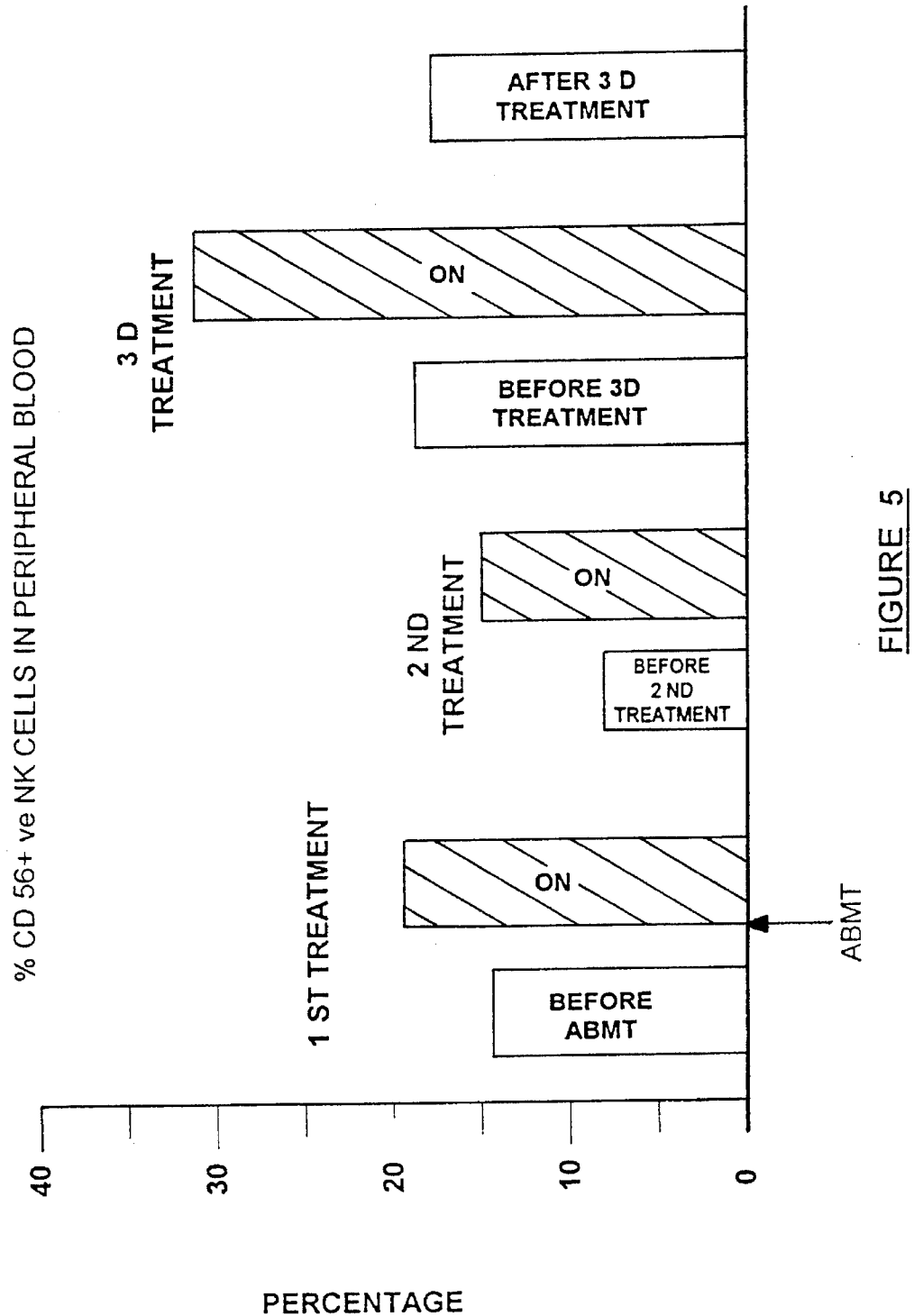
FIG. 5: Frequency of CD 56 positive cells in peripheral blood of patient 1 before and at different time after autologous bone marrow transplantation. on=at the end of a 3 week Linomide treatment, off=at the end of a 3 week treatment free interval.
Figure 6:
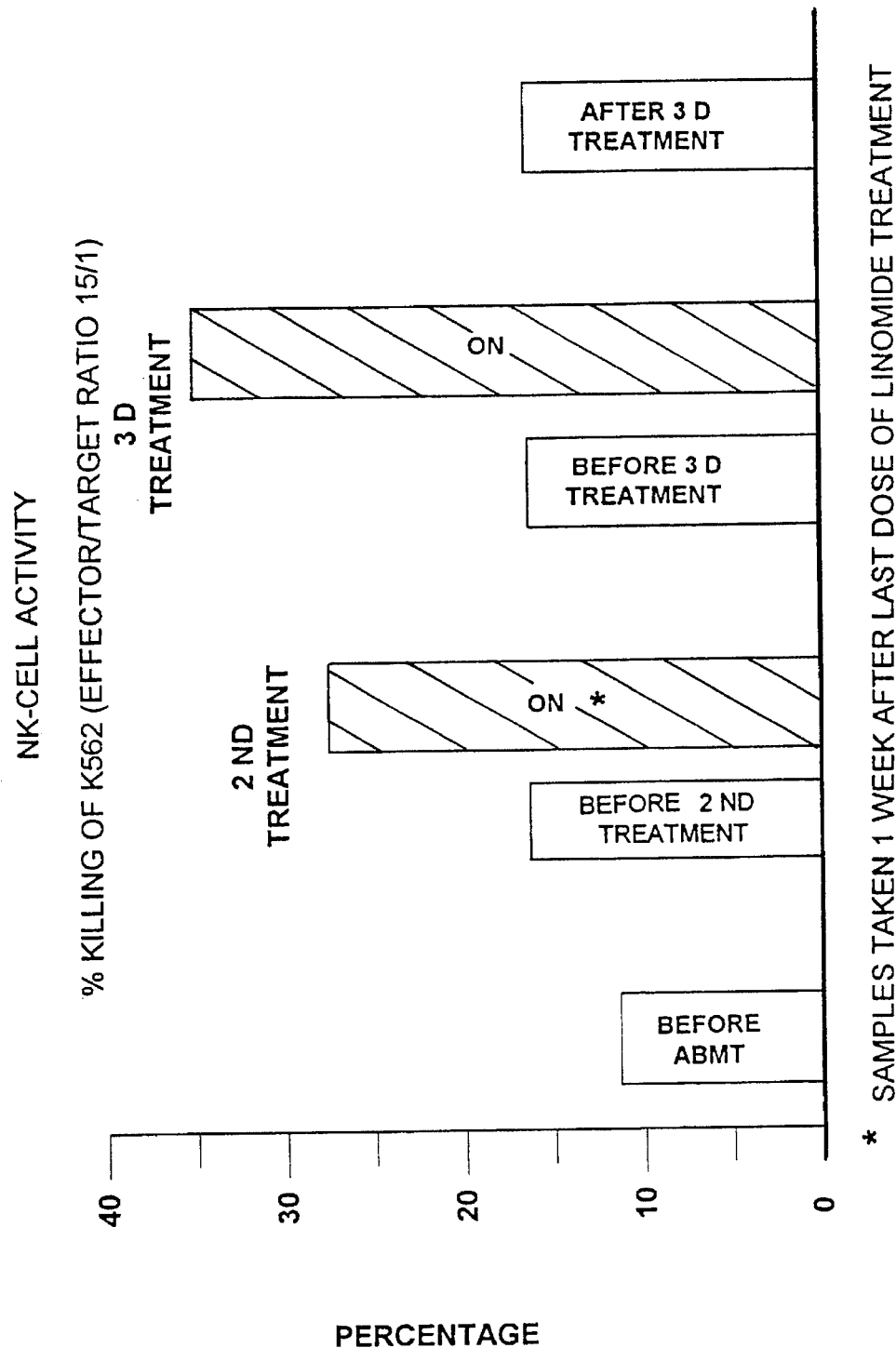
FIG. 6: Cytotoxic activity against K-562 of peripheral blood lymphocytes from patient 1 before and at different time after autologous bone marrow transplantation. on=at the end of a 3 week Linomide treatment, off=at the end of a 3 week treatment free interval. Effector:target ratio 15:1.

1. Larsson, E. L., Joki, A. L. and Stålhandske, T.: Mechanism of action of the new immunmodulator LS 2616. Int. J. Immunopharmacol. 9:425, 1987.
2. Kalland, T., Alm, G., and Stålhandske, T.: Augmentation of mouse natural killer cell activity by LS 2616, a new immunomodulator. J. Immunol. 134:3956, 1985.
3. Stålhandske, T., and Kalland, T.: Effect of the novel immunomodulator LS 2616 on the delayed-type hypersensitivity reaction to *Bordetella pertussis* in the rat. Immunopharmacol. 11:87, 1986.
4. Tarkowski, A., Gunnarson, K., and Stålhandske, T.: Successful treatment of autoimmunity in MRL/l mice with LS 2616, a new immunmodulator. Arthritis and Rheum. 29:1405, 1986.
5. Kalland, T.: Effects of the immunomodulator LS 2616 on growth and metastatis of the murinne B16-F10 melanoma. Cancer Res. 46:3018, 1986.
6. Kalland, T.: Interleukin 3 is a major negative regulator of the generation of natural killer cells from bone marrow precursors. J. Immunol. 137:2268, 1986.
7. Bengtsson, M., Tötterman, T. H., Smedmyr, B., Festin, R., Öberg, G. and Sominnsson, B.: Regeneration of functional and activated NK and T subset cells in the marrow and blood after autologous bone marrow transplantation: A prospective study with ⅔-color FACS analysis. Leukemia 3:68, 1989.

We claim:

1. A method for increasing the frequency of bone marrow NK cell precursors comprising administering to a patient a therapeutically effective dose of N-phenyl-N-methyl-1,2 dihydro-4 hydroxy-1-methyl-2-oxo-quinoline-3-carboxamide or an acceptable salt thereof.

2. The method of claim 1, wherein administration is oral.

3. The method of claim 2, wherein the administration is parenteral.

4. The method of claim 1, wherein the administration is by injection.

5. The method of claim 1, wherein the therapeutically effective amount ranges from 0.01 to 10.0 mg/kg body weight.

6. The method of claim 1, wherein the therapeutically effective amount ranges from 0.05 to 1.0 mg/kg body weight.

7. The of claim 1, wherein the therapeutically effective amount ranges from 0.2 to 0.3 mg/kg body weight.

8. The method claim 1, wherein the administration is daily for an effective period.

9. The method of claim 1, wherein the administration is bi-weekly for an effective period.

10. The method of claim 1, wherein the administration is bi-monthly for an effective period.

11. The method of claim 1, wherein the effective dose is dispersed within a pharmaceutically acceptable carrier.

12. A method for accelerating bone marrow cell recovery after bone marrow transplantation comprising administering to a patient who as received a bone marrow transplant a therapeutically effective dose of N-phenyl-N-methyl-1,2 dihydro-4 hydroxy-1-methyl-2-oxo-quinoline-3-carboxamide or an acceptable salt thereof, which therapeutically effective dose increases the frequency of bone marrow NK cell precursors.

13. A method for accelerating bone marrow recovery from anti-neoplastic drug treatment comprising:

administering to a patient who has received anti-neoplastic drug treatment which is toxic to hemopoietic cells, a therapeutically effective dose of N-phenyl-N-methyl-1,2 dihydro-4 hydroxy-1-methyl-2-oxo-quinoline-3-carboxamide or an acceptable salt thereof, which therapeutically effective dose increases the frequency of bone marrow NK cell precursors.

14. A method for accelerating bone marrow recovery from irradiation treatment comprising administering to a patient who has received irradiation treatment which significantly impairs hemopoietic cells, a therapeutically effective dose of N-phenyl-N-methyl-1,2 dihydro-4 hydroxy-1-methyl-2-oxo-quinoline-3-carboxamide or an acceptable salt thereof, which therapeutically effective dose increases the frequency of bone marrow NK cell precursors.

* * * * *